United States Patent [19]

Engelhardt

[11] Patent Number: 4,652,459

[45] Date of Patent: Mar. 24, 1987

[54] IMPLANTS, AND PROCESS FOR THE PRODUCTION THEREOF

[76] Inventor: Achim Engelhardt, Donnersbergstrasse 42, D-6000 Frankfurt/Main, Fed. Rep. of Germany

[21] Appl. No.: 761,078

[22] Filed: Jul. 31, 1985

Related U.S. Application Data

[62] Division of Ser. No. 549,791, Nov. 7, 1983, Pat. No. 4,525,412.

[30] Foreign Application Priority Data

Nov. 10, 1982 [DE] Fed. Rep. of Germany ....... 3241589

[51] Int. Cl.$^4$ .................. A01N 1/02; B05D 1/36; B05D 7/00; A61F 5/04
[52] U.S. Cl. ................. 427/2; 128/DIG. 21; 427/309; 427/354; 427/407.2; 427/414; 623/16; 623/18
[58] Field of Search ................... 106/124, 207, 287.16; 128/92 R, 92 C, DIG. 8, DIG. 21; 427/2, 255, 402, 407.2, 414, 354, 309; 623/11, 16, 18, 66

[56] References Cited

U.S. PATENT DOCUMENTS 3,808,113 4/1974 Okamura et al. .......... 204/159.13 X

*Primary Examiner*—Michael R. Lusignan
*Attorney, Agent, or Firm*—Michael J. Striker

[57] ABSTRACT

An improved implant is disclosed, having a customary substrate, particularly at least partially of metal, and a one- or multi-layer coating of ceramic, biologically compatible glasses and/or bioactive glasses, the improvement comprising a second type layer covalently bound on said coating of ceramic or bioglass said second type of layer being from polymeric organo-silicon compounds, and said second type of layer being covalently coupled, with or without a coupling molecule, with a third type of layer of a synthetic or natural biopolymer. Also disclosed is a process for producing the implant, by applying in known mariner a coating of ceramic, biologically compatible and/or bioactive glasses onto a substrate of said implant, providing said coating with a second type of layer of polymerized organo-silicon compound (polysiloxane) in covalent connection therewith, and coupling said second type of layer with a third type of layer of a synthetic or natural biopolymer, with or without use of a coupling means.

10 Claims, No Drawings

IMPLANTS, AND PROCESS FOR THE PRODUCTION THEREOF

This is a division of application Ser. No. 549,791, filed Nov. 7, 1983, now U.S. Pat. No. 4,525,412.

BACKGROUND OF THE INVENTION

By the term "implants" is understood artificial organ parts, which assume their functions or partial functions temporarily or permanently in human or animal bodies. Joint replacement parts, skeleton replacement parts, tumor prosthetics, tooth replacements, such as implantable teeth, or similar parts of the human or animal body, are involved.

Known implantations of the above-mentioned type are composed in many cases, completely or partially, of metal, particularly high-duty or refined steel. It is, however, also possible to use in particular the following materials: glass ceramic, sintered ceramic, osteoceram materials, various types of glass (particularly in the form of coatings for metal), alone or worked together, for the construction of implants.

It is known that with metal implants particularly the disadvantage of insufficient corrosion and stress corrosion resistance of the metal against the fluids and secretions of the living body, as well as the insufficient abrasion resistance with implant parts conducted relative to one another, are problems which arise in use. Metallic particles possess the danger that they will be led into the surrounding tissue and imbed themselves there, which can lead to very serious injuries, such as for example the appearance or manifestation of irritations, and stiffening of joints, and which decrease the service life of the implants.

For these reasons, metallic implants have been developed which are coated completely or partially with enamel. Such implants are described, for example, in German Offenlegungsschrift No. 23 40 546. Correspondingly, particular embodiments of such implants can possess a coating of partially crystallized enamel, and they can also be provided with multi-layered application of enamel, whereby if necessary, a partially crystallized base enamel can be located on the base metal. With such a multi-layered application of enamel it is advantageous to provide a glassy covering enamel. In each case it is preferred that the enamel surface be locally profiled, for example by mechanical or chemical roughening or by means of engraving of indentations.

It has, however, turned out that the connection between implant and the tissue which surrounds the implant after placing it in the body of the human or animal patient, is still in need of improvement. Therewith it is to be considered that the connection between implant and tissue should exclude relative movements within limit ranges. This connection is, in addition, to be so provided that the biophysical control system of the tissue, injured or broken as a result of the operation, be reinstated or restored as much as possible to its specific impulse patterns, which in all cases represent regulating stimuli for growth and maintenance of the tissue, by means of material-determined connection. Therewith it is moreover to be considered, that through construction and chemical state of the surface, occurring mechanical forces be distributed and transferred in optimal manner to the bones. Although also different bioelectrical and biochemical characteristics (e.g. piezoelectric city and surface groupings of bone collagens and current potential in the osteone system) intervene, which according to previous knowledge contribute to variations in bone material, these should be as well compensated or maintained as possible with implants.

SUMMARY OF THE INVENTION

The present invention is therefore based upon the object of not only preserving the advantages of the known implants with enamel coatings (such as resistance to wear and tear and corrosion, and great constructive freedom with the design of the implant), but in other respects to also still substantially improve the connection of the implant with the anchoring tissue. Therewith should remain extensively preserved, mainly by means of physiologically adapted introduction of force, particularly though also by means of chemical surface modifications, macroscopic and preferably also submicroscopic relative movements within the limiting range between implant and surrounding tissue, otherwise pre-osseous, non-mature tissue formations, unsuitable for transfer of force, will form, instead of the prerequisite mature bones.

The subject of the invention is therefore an implant from a customary substrate, preferably at least partially of metal, and a one- or multi-layer coating of ceramic or biologically compatible glass and/or bioactive glass, which is thereby characterized in that there is coupled to the coating of ceramic or bioglass an additional, covalently bound layer of a polymeric organo-silicon compound, which with or without a coupling molecule is covalent with a further layer of a synthetic or natural biopolymer, preferably a polypeptide.

The substrate or base material is very precise in its design and its mechanical-physical characteristic valves, and surely adjustable to the requirements of the specifically provided instance of use. To the extent that an implant is supposed to be manufactured with relatively small dimensions and complicated shapes, for example with sharp corners or edges, roundness of small radius, etc.; it is recommended to employ as substrate a material with a low coefficient of linear expansion.

The term "bioglass" as used in this specification is to be understood to mean glass materials which, in known manner, can be used in the biological area, particularly for implants.

It has already been referred to that also suitable materials of ceramic or bioglass are known for a one- or multi-layer coating of the substrate, as well as expedient methods for their production.

In general, the portion of silicon compounds in the ceramic or glass material should lie in a range from at least 40% by weight in particular from 50 to 100% by weight.

Glass materials thus coming into consideration include for example, quartz glass, borosilicate glasses, lime-sodium glasses, and as glass ceramics, partially or completely crystallized glasses or enamels. Clay materials (produced from principally kaolin-containing masses) or stoneware, for example, can be used as sinter ceramics.

The implant, provided with a coating of ceramic or bioglass, is then activated at the surface, i.e. in order to provide an optimal number of —Si—OH-groups at the surface before the treatment with the polymeric organo-silicon compound.

In particular when polished glass or ceramic surfaces are provided on the coated substrate, it is expedient to pre-etch these with hydrogen fluoride, and to subsequently hydrolyse them with pure water. This treatment can thereby be undertaken by allowing 10% hydrogen fluoride to work itself in. Independent from the quality or condition of the glass or ceramic surface, the following manner of operation is expedient for its activation:

All surfaces are cleaned in a dust-free, oxygen-free room with the following ultrafiltrated, de-gasified solvents: acetone, toluene, ethanol and double-distilled water. Thereupon the fat- and dust-free surfaces are dried in known manner with a vapor stream of an organic solvent which forms with water an azeotropic mixture. Then follows an oxidative hydrolysis of the surface with 1–3M nitric acid, which should be allowed to work itself in for three hours at room temperature. There follows then a washing stage with diluted hydrochloric acid and then with pure water. Thereafter one can follow with an acid hydrolysis in a water bath at increased temperatures (for example at 70° C. for about 5 to 10 hours). For this purpose it is expedient to proceed with ortho-phosphoric acid, acetic acid, perchloric acid or hydrochloric acid preferably at a strength from 1 to 3 m, whereupon a brief watering follows, with water.

After this has been done, a further alkaline hydrolysis is performed with heated caustic soda or potash lye. With an alkali-concentration from 0.5 to 3 m, a temperature of 70° C., for example, can be used, and the hydrolysis is performed over a period of 24 hours.

A subsequent treatment follows expediently with ultrafiltrated, doubly-distilled water.

The aim of the prescribed treatment of the surface of the glass or ceramic coating is to obtain an as extensive as possible, preferably quantitative, hydrolytic splitting of the surface oxides. Therewith arise silanol groups ≡Si—OH or ≡Si—O-alkali.

Obviously, known methods suitable for this purpose can be employed collectively, particularly the hydrolysis with acids and/or alkalis. Such processes can each be selected according to the specific case provided, e.g. the type of glass or ceramic material, without requiring inventive thought, by the expert.

The activated glass or ceramic surface is then treated with a polymerisate of an organo-silicon compound, e.g. based upon a di- or tri-alkoxysilane or a mixture thereof, whereby the organic residue is coupled covalently to the silanol groups of the surface. Preferably, this organo-silicon compound contains alkylamino- and/or alkylhalogenide groups, and/or glycid-oxy- or glyceryl-groups, particularly those having 1 to 4 carbon atoms. The type of the produced compounds, e.g. monomeric layers or more or less cross-polymerized polymeric space structures of pure polymer or mixed polymer, is not critical to the invention. However, it is preferred for there to be produced an as-solid-as-possible connection between the surface of the silicate raw material and the organo-silicon compound.

The arising surface groups are convertable into an activated form by means of customary processes of preparative organic chemistry, particularly reduction or oxidation and can be coupled with body-compatible organic polymers or even filaments.

The novel features which are considered as characteristic for the invention are set forth in particular in the appended claims. The invention itself, however, both as to its construction and its method of operation, together with additional object and advantages thereof, will be best understood from the following description of specific embodiments.

DESCRIPTION OF THE PREFERRED EMBODIMENTS

Correspondingly, a preferred embodiment of the present invention employs as organo-silicon compounds (silane), diakoxyalkyl- or tri-alkoxy silane, or their mixtures, particularly of the general formula $$(R^1O)_3Si{-}R^2 \text{ or } (R^1O)_2SiR^2R^3,$$

wherein $R^1$ and $R^3$ are independently alkyl, particularly with 1 to 4 carbon atoms, e.g. with 1 to 2 carbon atoms, and $R^2$ is a straight- or branched-chain aminoalkyl-, alkylhalogenide-, thiol-, or either alkyl or glycid-oxy substituted with several hydroxyl groups, particularly with 2 to 5 carbon atoms.

For silanization, good results are obtained using the following organo-silicon compounds, in pure form or as mixtures:

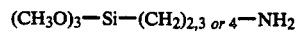

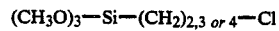

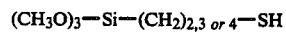

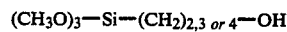

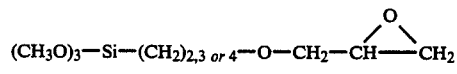

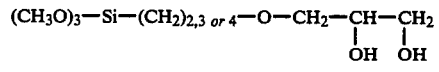

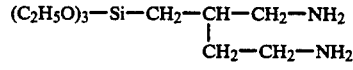

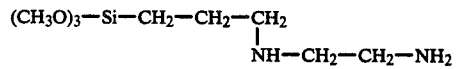

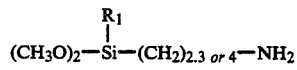

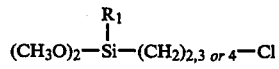

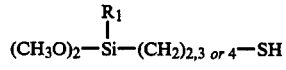

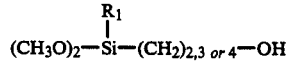

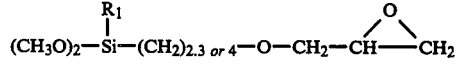

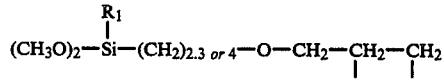

-continued

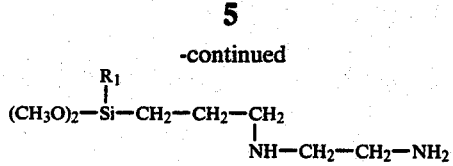

The entire list, with the linking molecule part

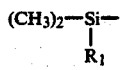

again with $R_1 = CH_3$, $-C_2H_5$, -phenyl.

In the above-given organo-silicon compounds, obviously the provided methoxy- or ethoxy-groups can be replaced by other alkoxy groups, i.e. thus by methoxy, ethoxy, propoxy or butoxy groups.

The silanization follows expediently under a dust-free atmosphere, whereby one of the following three processes, indeed according to the desired layer thickness and layer quality, can be employed:

1. Gas phase coating (provides homogeneous, thinner layers).

The contaminated activated surfaces of the glass or ceramic material are treated in a reactor of Duran glass, if necessary under an inert atmosphere, with vapors of a mixture of 1 to 2 parts by volume of the organo-silicon compound of an aprotic, heavily polar solvent, with heating. The heat supply is so regulated, that the surfaces to be treated are completely exposed to the vapor of silane and solvent for about 16 to 20 hours. As solvent, for example toluene, xylene, tetrahydrofuran, chloroform, or dioxane can be employed. Thereupon, the silanized surfaces are preferably subjected to multiple washings and drying.

2. Coating in organic solvent (provides thicker, somewhat less homogeneous layers, then the previously mentioned example 1).

The activated surfaces are, as above, silanized with a mixture of 5 to 15% of the silane in the solvent, under addition for 2 hours of stoichiometric amounts of water, for 16 to 20 hours under stirring.

3. Coating in acid, aqueous solution with evaporation of the solvent (provides stable, thick polymer layers).

The silane, before the coating reaction, is slowly and with stirring, so dripped into fresh distilled water, after pH-adjustment according to customary chemical techniques with 0.1M NaOH or 0.1M HCl, that the pH remains between 5.5 and 6.0, and a 5 to 10% aqueous solution is produced.

Thereupon, the mixture is quickly heated to 90° C., and the material to be coated is left in the solution, with light stirring. Then, it is washed with fresh water, alcohol and acetone, and dried at 110° C. This washing treatment is useful with all silanized surfaces.

According to the present invention it has now been discovered that the so-obtained terminal amino-, sulfhydryl-, halogen-, glycidoxy-, or hydroxyl-groups of the silicon organic compound are suitable for coupling to the treated glass or ceramic layer of the implant (directly or after chemical modification of the groups through reduction, oxidation or substitution) with structural proteins or similar polypeptides across an amide-, peptide-, imino-, disulfide-, ether- or other type of covalent bond.

Expediently, the following may be referred to, by way of example, as peptide materials: base building blocks, partial sequences or mixed fractions particularly of natural peptides from the class of Type I Collagen (skin, eye or bone collagen). As amino acid sequences one can employ, for example, amino acid triplets, which contain e.g. glycine, proline, hydroxyproline and/or alanine groups, whereby preferably the glycine group is terminal. Moreover, combinations of these triplets are possible, with good results, such as e.g. corresponding hexa- and nona-peptides.

According to another embodiment of the present invention, one can employ as polypeptide those having an $\alpha$ 1-chain or its bromo-cyano-cleavage product (CNBr-peptide).

However, also specific growth and differentiation factors (osteoinductive factors) or other non-structural proteins or glycoproteins and proteoglycanes are suitable for coupling.

For construction of the polypeptide chains under formation of peptide bonds between a C-terminal protected, N-terminal free amino acid and a Boc-protected, C-terminal free amino acid or a peptide, the following processes are suitable:

0.1M of the C-terminal free peptide are suspended in 400 ml of a suitable solvent, such as dichloromethane or dioxane or THF, and cooled down to 0° C. Then, the following are successively added:

13.51 g (p.1M) N-hydroxy-benzotriazol (HOBt)

30.94 g (0.1 m M) dicyclohexyl-carbodiimide (DCC) or diisopropyl-carbodiimide.

Subsequently, 0.1M of the N-terminal free amino acid or a corresponding amount of the surface-coating material is added, and stirred for one hour at 0° C. and three hours at room temperature. Thereupon the dichloromethane or the corresponding solvent is completely spun in and the residue withdrawn in 500 ml acetic ester. For separation of the urea produced by the reaction it is repeatedly rinsed with solvent and the solvent is thereupon filtered.

The coated surface is washed several times with 5% citric acid solution, saturated sodium chloride, 5% sodium bicarbonate and again saturated sodium chloride solution, and then dried across sodium sulfate. For further separation of the dicyclohexyl- or diisopropyl-urea, the surface is rinsed with ethyl acetate.

In another, principally similar type of the peptide-coupling, the carrier-bound carboxyl group is completed with a C-terminal protected peptide according to the above-given process.

In a third process, for example the free amino group of the silane covalently bound to the glass ceramic with about 40 cm² surface is reacted by means of 18-hours' stirring at room temperature in 100 ml (0.25%) freshly purified glutaraldehyde solution into Schiff base with freer aldehyde function. After the washing with 1 to 2 liter fresh water, a production of reconstituted collagen fibers is obtained on the surface by means of immersing the surface, briefly dried in a vacuum desiccator, in a 0.8% solution of Type I collagen (beef fibers) in phosphate buffer (pH 8.0) with 0.165 Mol NaCl and 0.024 Mol $K_2HPO_4$. After washing in liberal amounts of water, the surface is reduced with 6 Mol $NaBH_3CN$ in 100 ml aqueous solution for stabilization of the newly formed Schiff base from surface groups and peptide.

According to need, the collagen layer is fixed by means of 6 to 8 hours immersion in 0.25% aqueous glutaraldehyde solution. This is followed by a careful washing with distilled $H_2O$, acetone, DMSO and vacuum drying. The so-coated surfaces can be sterilized with 180° C. hot air for 30 minutes.

In a further process, the glycidoxypropyl group produced on the surface by silanization is reacted through nucleophilic attack of an —SH, NH$_2$ or —OH group, for example from a side-chain of a peptide, at a pH-value between 8 and 10 (phosphate buffer).

In another embodiment of the same process, the glycidoxy group is hydrolysed into a glyceryl group on about 50 cm$^2$ of surface by means of one hours' stirring at room temperature with 100 ml of $10^{-3}$M HCl. The same surface is washed with water and agitated with 50 ml 0.1M NaIO$_4$ in water for two hours at room temperature. After the washing with water, the produced aldehyde function is reductively coupled, e.g. with the amino group from the side-chain of a peptide.

For this, about 50 cm$^2$ surface is slowly stirred with 20 mg peptide in 100 ml 0.2M phosphate buffer of pH 6.0, with 1 mM NaBH$_3$CN, for four days at room temperature. After the washing, non-reacted aldehyde functions can be removed through reduction with 1 ml 0.5M NaBH$_4$ at 4° C. (15 hours).

Through the described coupling process one succeeds, proceeding from various basic functions of the glass matrix, in covalently fixing peptide or structural protein or fragments thereof, or even glycoproteins (proteoglycane) onto the surface.

The so-obtained implants can be employed equally or in similar manner as the corresponding known implants.

It will be understood that each of the elements described above, or two or more together, may also find a useful application in other types of implants differing from the types described above.

While the invention has been illustrated and described as embodied in implants, and process for the production thereof, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Process for production of an implant, comprising
    applying a coating of ceramic, biologically compatible or bioactive glasses onto a substrate composed at least partially of metal,
    applying onto said coating a second type of layer of polymerized organo-silicon compound (polysiloxane) in covalent connection therewith, and
    applying onto said second type of layer a third type of layer of a synthetic or natural bipolymer in covalent connection therewith.

2. Process according to claim 1, further comprising before said step of applying onto said coating a second type of layer,
    cleaning said coating in a dust-free and oxygen-free area with ultrafiltrated, de-gasified solutions of acetone, toluene, ethanol and doubly-distilled water, thereby providing a fat-free and dust-free surface,
    drying said fat-free and dust-free surface with a vapor stream of an organic solvent which forms with water an azeotropic mixture,
    oxidatively hydrolysing said dry surface with 1 to 3M nitric acid,
    washing said surface with dilute nitric acid and then with pure water, and
    acid hydrolysing said surface in a water bath at high temperature, followed by briefly washing said surface with water.

3. Process according to claim 1, wherein said third type of layer of a synthetic or natural biopolymer is applied onto said second type of layer in covalent connection with use of a coupling means.

4. Process according to claim 1, wherein a polypeptide is employed as said natural or synthetic biopolymer.

5. Process according to claim 1, wherein said coating of ceramic or glasses comprises a polished surface, and further comprising pre-etching said surface with hydrogen fluoride and then hydrolizing with pure water.

6. Process according to claim 5, using for said pre-etching 10% hydrogen fluoride at room temperature.

7. Process according to claim 2, wherein said oxidatively hydrolysing is performed for about three hours at room temperature.

8. Process according to claim 2, wherein said acid hydrolysing is performed at about 70° C. with an acid selected from the group consisting of ortho-phosphoric acid, acetic acid, perchloric acid and hydrochloric acid, at a strength from 1 to 3M.

9. Process according to claim 2, further comprising before said step of applying onto said coating a second type of layer and after said brief washing,
    further alkaline hydrolysing said surface with heated sodium lye or potassium lye, and then washing with double-distilled water.

10. Process according to claim 9, wherein said lye is employed at a concentration from 0.5 to 3M.

* * * * *